(12) United States Patent
Scholling

(10) Patent No.: US 8,971,486 B2
(45) Date of Patent: Mar. 3, 2015

(54) SYSTEM AND METHOD FOR X-RAY INSPECTION

(75) Inventor: Axel Scholling, Wambach (DE)

(73) Assignee: Smiths Heimann GmbH, Wiesbaden (DE)

(*) Notice: Subject to any disclaimer, the term of this patent is extended or adjusted under 35 U.S.C. 154(b) by 553 days.

(21) Appl. No.: 13/235,123

(22) Filed: Sep. 16, 2011

(65) Prior Publication Data

US 2012/0069964 A1   Mar. 22, 2012

Related U.S. Application Data

(60) Provisional application No. 61/384,230, filed on Sep. 17, 2010.

(51) Int. Cl.
| | | |
|---|---|---|
| G01V 5/00 | (2006.01) | |
| G01N 23/02 | (2006.01) | |
| G01N 23/20 | (2006.01) | |

(52) U.S. Cl.
CPC .............. *G01V 5/0016* (2013.01); *G01N 23/02* (2013.01); *G01N 23/20083* (2013.01)
USPC ............................................ 378/57; 378/146

(58) Field of Classification Search
USPC .................................................. 378/57, 146
See application file for complete search history.

(56) References Cited

U.S. PATENT DOCUMENTS

| | | | |
|---|---|---|---|
| 2005/0089137 A1 | 4/2005 | Toth et al. | |
| 2009/0147911 A1* | 6/2009 | Joosten et al. | 378/7 |
| 2009/0232269 A1* | 9/2009 | Hsieh et al. | 378/5 |
| 2009/0245459 A1* | 10/2009 | Goto et al. | 378/16 |
| 2011/0002440 A1* | 1/2011 | Gatten et al. | 378/19 |
| 2011/0274249 A1 | 11/2011 | Gray et al. | |

FOREIGN PATENT DOCUMENTS

| | | |
|---|---|---|
| WO | WO 2004/015405 A1 | 2/2004 |
| WO | WO 2010/044774 A1 | 4/2010 |
| WO | WO 2012/035440 A2 | 3/2012 |

OTHER PUBLICATIONS

International Search Report mailed Apr. 3, 2012, in corresponding International Application No. PCT/IB2011/002752 (8 pages total).

* cited by examiner

*Primary Examiner* — Hoon Song
(74) *Attorney, Agent, or Firm* — Finnegan, Henderson, Farabow, Garrett & Dunner, LLP

(57) ABSTRACT

Methods and systems for x-ray inspection are provided. The system can include a source of radiant energy configured so that the radiant energy traverses a scanning volume. The system can further include a filter between the source and the scanning volume, a conveying apparatus configured to impart relative motion between an exposure-limited subject and the scanning volume, a conveyance monitor configured to generate conveyance data reflecting a conveyance state of the exposure-limited subject, a radiant energy sensing apparatus configured to sense radiant energy from the source and to generate source radiant energy data, and a dose controller configured to acquire conveyance data, source radiant energy data, and a signal related to subject dose data, and to generate a measure that a portion of the exposure-limited subject has acquired a dose of radiant energy above a dose threshold.

51 Claims, 5 Drawing Sheets

SYSTEM AND METHOD FOR X-RAY INSPECTION

CROSS REFERENCE TO RELATED APPLICATION

This application claims the benefit of U.S. Provisional Application No. 61/384,230, filed Sep. 17, 2010, the content of all of which is incorporated herein by reference.

FIELD

The present disclosure relates generally to systems and methods for x-ray inspection, more particularly, to a system providing x-ray screening of human subjects.

BACKGROUND

X-ray inspection systems can be used for screening individuals, baggage, and cargo at security checkpoints. For example, x-ray inspection systems can permit the identification of concealed contraband items, such as, weapons, explosives, and illicit drugs. When used for screening individuals, the use of x-ray inspection systems can increase the individual's annual effective dose, where a "dose" of radiant energy is a measure representative of the amount of radiant energy absorbed by an individual.

SUMMARY

In one aspect, the present disclosure is directed to a system configured to expose a target to x-ray radiation. The system can include at least one source of radiant energy, where at least a first portion of the radiant energy can lie within an x-ray spectrum, and where the source can be configured so that the first portion of the radiant energy traverses at least a portion of a scanning volume. The system can further include a filter situated between the source and the portion of the scanning volume, a conveying apparatus configured to impart relative motion between an exposure-limited subject and the portion of the scanning volume, and a conveyance monitor configured to generate conveyance data reflecting at least a conveyance state of the exposure-limited subject. In addition, the system can include a first radiant energy sensing apparatus configured to sense radiant energy from the source and to generate source radiant energy data and a dose controller configured to acquire conveyance data, source radiant energy data, and a signal related to subject dose data, and to generate a measure that at least a portion of the exposure-limited subject has acquired a dose of radiant energy above a dose threshold.

An additional aspect of the present disclosure is directed a method for scanning an exposure-limited subject. The method can include producing at a source, radiant energy within a defined x-ray spectrum, providing the radiant energy in a direction that traverses at least a portion of a scanning volume, filtering the radiant energy with a filter, applying at least a portion of the radiant energy to the scanning volume, and conveying the exposure-limited subject to the scanning volume and generating conveyance data indicative of at least a conveyance state of the exposure-limited subject. The method can further include applying at least a portion of the filtered radiant energy to the exposure-limited subject, sensing the radiant energy produced from the source and generating source radiant energy data. In this aspect, the method can further include acquiring conveyance data, source radiant data, and a signal related to subject dose data at a dose controller and generating a measure indicative of the dose of radiant energy acquired by the exposure-limited subject, where the measure indicates when the exposure-limited subject has acquired a dose of radiant energy above a dose threshold. The method can further include adjusting at least one of the production of radiant energy, the filtering of radiant energy, and the conveying in response to at least one of the conveyance data, source radiant data, and the signal related to subject dose data, and the measure.

Additional objects and advantages of the disclosure will be set forth in part in the description which follows, and in part will be obvious from the description, or can be learned by practice of embodiments consistent with the disclosure. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the disclosure and together with the description, serve to explain the principles of the disclosure. In the drawings.

DESCRIPTION OF THE EMBODIMENTS

Reference will now be made in detail to the present exemplary embodiments, an example of which is illustrated in the accompanying drawings. Wherever possible, the same reference numbers will be used throughout the drawings to refer to the same or like parts.

Figure 1:
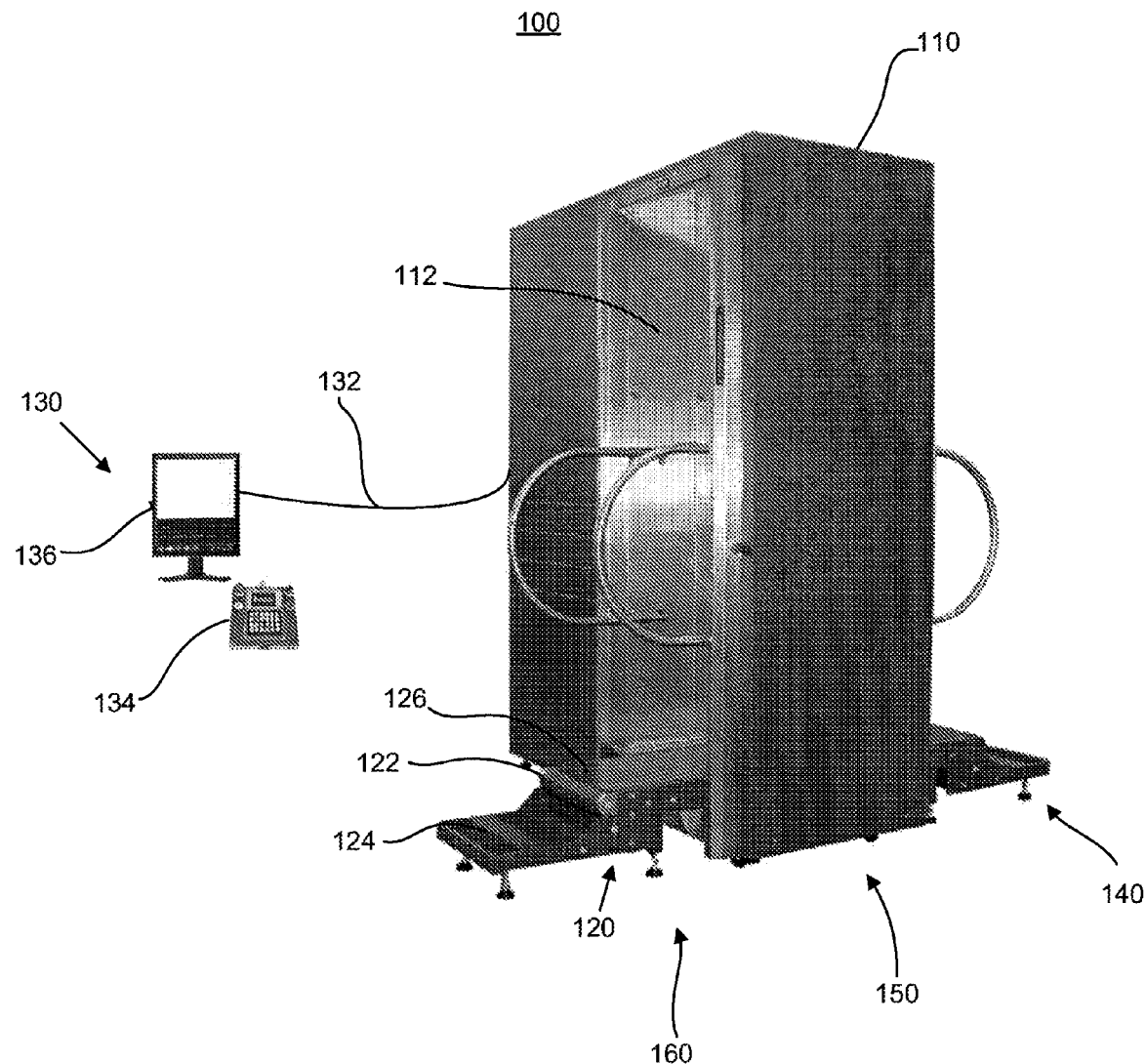
FIG. 1 is a schematic diagram of an inspection system consistent with an exemplary embodiment of the present disclosure.

FIG. 1 is a schematic diagram of an inspection system 100 according to an exemplary embodiment of the present disclosure. An exemplary embodiment of the inspection system 100 can be configured to screen an individual to detect any material or object of interest that may be obscured from view or otherwise concealed. The individual can have a concealed material or object of interest on or in their person, where the object of interest can include, for example, contraband items, weapons, incendiaries, illicit drugs, radioactive materials, or explosives, such as, but not limited to an improvised explosive device, liquid explosive material, plastic explosives, and the like. In an embodiment, the inspection system 100 can be employed at a security check point at a detention center for screening inmates. Alternatively, in an embodiment, the inspection system 100 can be used at an airport or other transportation terminal where it can be necessary to detect objects of interest or materials concealed on individuals.

Inspection system 100 can include a radiation scanner 110, a conveyance apparatus 120, and a data processor 130 coupled to the radiation scanner 110 and the conveyance apparatus 120.

The radiation scanner 110 can include at least one source of radiant energy, a sensing apparatus, and a dose controller. Source and sensing apparatus can be mounted, stationary, on both sides of an inspection compartment 112 through which an individual can be conveyed. The inspection compartment 112 can be of any suitable shape, including for example, rectangular, square, circular, oval, or U-shaped. It is contemplated that the inspection compartment 112 can be configured to accommodate individuals of varying heights, weights, and physical ability.

A source apparatus consistent with the present disclosure can generate x-ray radiation beam over a substantially two-dimensional cross-section through which an individual passes. At least a portion of the radiant energy associated with the x-ray radiation beam can pass through a portion of the inspection compartment 112. That portion of the radiant energy that passes through the inspection compartment 112 can define a scanning volume within the inspection compartment 112. Specifically, a scanning volume can be defined by that portion of the spatial volume within the inspection compartment 112 where at least a portion of the radiant energy associated with the generated x-ray radiation is configured to be present during scanning. In an embodiment, the scanning volume can be fixed spatially relative to the structure of the inspection compartment 112. It is contemplated, however, that a scanning volume does not necessarily have to be fixed relative to the structure of the inspection compartment 112, but can exhibit some motion, such as, for example, a scanning volume that, over time, repetitively passes through a larger region of space within the inspection compartment 112. As used herein, the region (or regions) that can be subject to a portion of the applied radiant energy within the inspection compartment 112 is (or are) referred to as the "scanning volume."

The source can be configured to generate radiant energy x-ray beams over a continuous range of energies, or configured to generate radiant energy x-ray beams at a single energy. The inspection system 100 can include multiple sources or a single source to generate the radiant energy. The energy of the x-ray sources can range, for example, from 120 kV to 300 kV. In an embodiment, the source can include a first radiation source, such as a 160 kV x-ray generator.

Figure 2B:
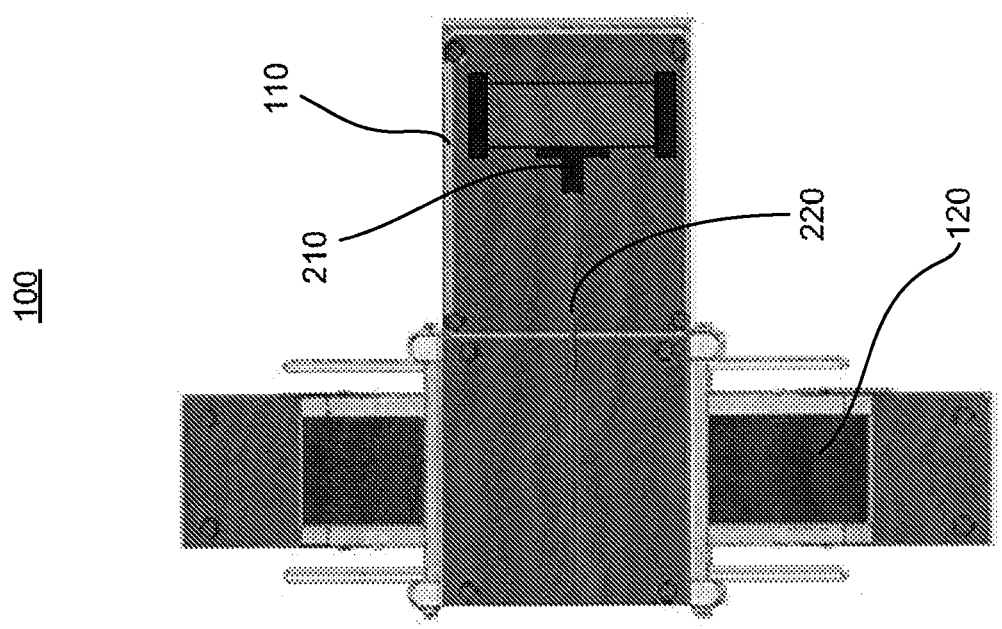
FIGS. 2A-2B depict a schematic diagram of an emitted x-ray beam consistent with an exemplary embodiment of the present disclosure.
Figure 2A:
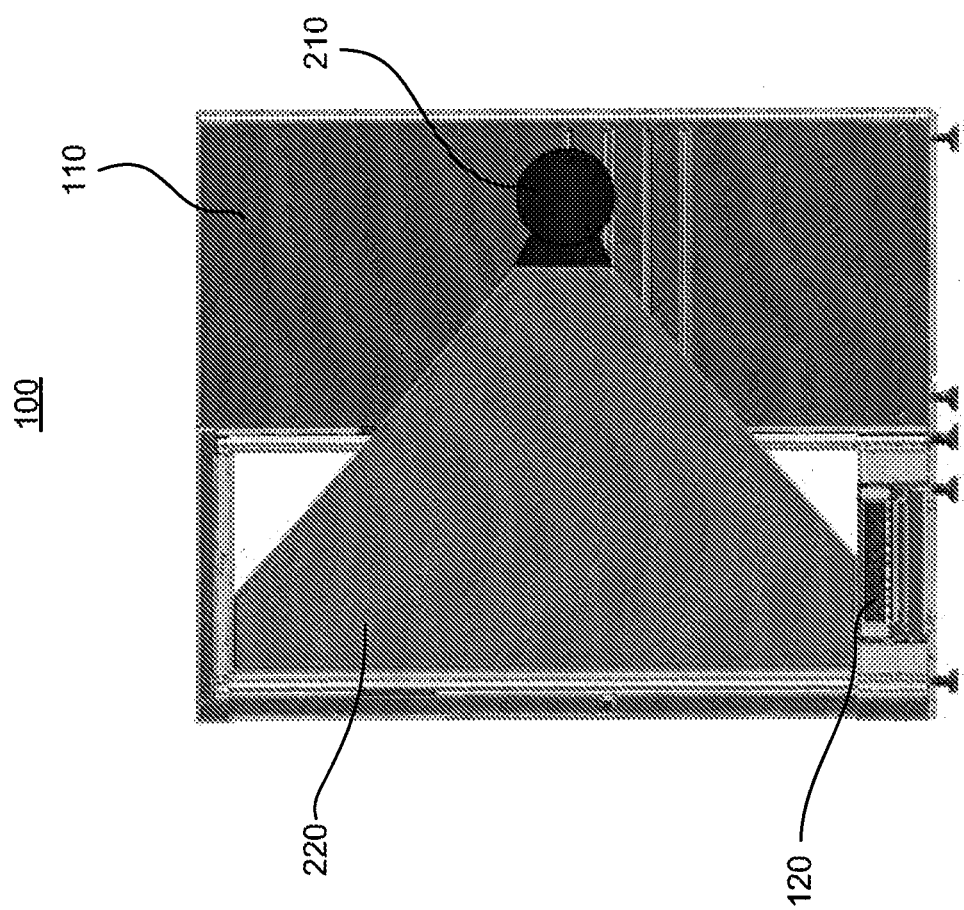

The x-ray beams can be shaped using a collimator. FIG. 2A provides a side view of the inspection system 100 and FIG. 2B provides as plan view of the inspection system 100. As illustrated in FIGS. 2A and 2B, the use of collimators 210 in the embodiment can shape the emitted x-rays into a into a narrow fan shaped beam 220. In an embodiment, the collimators 210 shape the emitted x-rays into a beam that traverses at least a portion of the inspection compartment 112. In an alternative embodiment, the collimators 210 can shape the emitted x-ray into a beam that traverses various portions of the inspection compartment 112. It is also contemplated that the collimators 210 can shape the emitted x-ray into a beam that traverses the entire inspection compartment 112. For example, the configuration of the collimators 210, inspection compartment 112, and the angle subtended by the fan-shaped beam depicted in FIG. 2A generate relatively small zones within inspection compartment 112 that are not traversed by the x-ray beam. In further embodiments, the configuration of the collimators 210, inspection compartment 112, and the angle subtended by the fan-shaped beam can reduce these regions more, and/or eliminate these regions entirely.

It has been found that a portion of inspection system 100 between the source of x-ray radiation and the inspection compartment, which can be a combination of glass, oil, epoxy, and titanium, aluminum, polyethylene, and stainless steel materials, can effectively function as a filter of low-energy x-ray radiation. (As used herein, the term "effective filter" will apply to such a portion of inspection system 100.) In an embodiment, a filter, which can include the effective filter of inspection system 100 and which can also consist entirely of the effective filter of inspection system 100, can be situated between the source and the scanning volume and can block low-energy radiant energy from reaching the individual within the scanning volume and/or the sensing apparatus. The filter, which can include the effective filter or consist entirely of the effective filter, can block some or all wavelengths of the spectrum of radiant energy generated by the source. By filtering the low-energy radiant energy the dose of x-ray radiation imposed on the individual being scanned can be reduced and image quality can be improved.

The combination of materials and the thickness of the materials that make up the filter, including the effective filter, can affect the filter's ability to block certain wavelengths of radiant energy. The filter can include material having a high atomic number in order to filter out low-energy radiant energy from the x-ray beam. In an exemplary embodiment, the filter (including without limitation the effective filter) can comprise a combination of materials, including, for example, glass, oil, epoxy, titanium, aluminum, polyethylene, and stainless steel. The radiation attenuation properties of the filter can be characterized using an aluminum equivalent. The aluminum equivalent of the filter can provide an approximation of the radiation attenuation of the filter in terms of the radiation attenuation caused by a corresponding layer of aluminum of a specified thickness.

Without limitation, the aluminum equivalent of the effective filter is the sum of the aluminum equivalents of each component of the inspection system 100 between the source and the inspection compartment. The aluminum equivalent for each component of the effective filter is the thickness of aluminum that would attenuate the x-ray beam by an amount equal to that provided by the component. In an embodiment, the aluminum equivalent of the effective filter can include, for example, the combination of the aluminum equivalents of the glass envelop of the x-ray tube, and other material components of the radiation scanner 110 between the source and the inspection compartment. The portion of the radiation scanner 110 between the source and the inspection compartment can include various materials including, without limitation, aluminum, stainless steel, and polyethylene. In an embodiment, where the energy of the x-ray source can be approximately 160 kV, the portion of the radiation scanner 110 between the source and the inspection compartment can include, for example, two layers of Aluminum of approximate thickness 0.5 (±approximately 0.05) mm, a layer of polyethylene of approximate thickness 3.0 (±approximately 0.3) mm, and a layer of stainless steel of approximate thickness 0.8 (±approximately 0.08) mm. Accordingly, where the energy of the x-ray source can be 160 kV, the aluminum equivalent of the effective filter can be between approximately 2.5 mm and approximately 1.5 mm. For example, in an embodiment with a 160 kV energy x-ray source, the aluminum equivalent of the effective filter can be approximately 2 mm. In other embodiments, and depending upon the energy of the x-ray source, aluminum equivalent of the effective filter can be greater than 2.5 mm or less than 1.5 mm.

In reference to FIG. 1, a conveying apparatus 120 can include a conveyor 122, steps 124, and a conveyance monitor (not shown). The steps 124 can include raised platforms for providing the individual to the conveyor 122 and the scanning volume. It is also contemplated that the steps 124 may include a ramp, motorized lift, or any other method of providing an individual to the conveyor 122. The conveyor 122 can include belts 126 and/or rollers for supporting the individual to be scanned as they are conveyed through the scanning volume. The conveyor 122 can further include one or more motors to drive belts 126 and/or rollers. The belts 126 and/or the rollers can operate intermittently or continuously to convey or provide the individual from an entry area 140, through a scanning area 150, to an exit area 160. It is contemplated that other forms of conveyors can be used. The conveyor 122 can be configured to vary the direction, speed, and acceleration of the motor and associated belt in accordance with conveyance instructions received from the dose controller. The conveyance monitor can be configured to generate conveyance data representative of a conveyance state of the individual through the scanning volume. The conveyance state can indicate the position and movement, i.e., direction and speed, of the individual with respect to the scanning volume.

In an embodiment, a sensing apparatus can be utilized to detect the emitted radiant energy. In addition, the sensing apparatus can be configured to detect reflected radiant energy. In an embodiment, a first radiant sensing apparatus can be configured to sense the radiant energy emitted from the source. Based on the sensed energy, the first sensing apparatus can generate source radiant energy data indicative of, for example, the energy level of the x-ray spectrum produced by the source.

In an embodiment, a second radiant sensing apparatus can also be configured to sense the radiant energy emitted from the source and transmitted through the individual within the scanning volume. Radiant energy can be directed towards the scanning volume and can be absorbed or attenuated by the body (or a portion of the body) of the individual in the scanning volume. The second sensing apparatus can be oriented such that its detection surface is directed towards the scanning volume. The frequency-dependent contributions to the radiant energy of the x-ray beam incident on the body of an individual can be absorbed and attenuated by the different density tissues and materials encountered as the contributions pass all the way, or part of the way, through the body. Bone, for example, is a relatively dense material within the body and can attenuate many contributions to the radiant energy of the x-ray beam. In contrast, soft tissue is relatively less dense within the body and can attenuate fewer of the contributions to the radiant energy of the incident x-ray beam. Therefore, as the individual passes through the scanner 110, a two-dimensional projection image of the individual's anatomy can be formed as a function of the x-ray energy from the two-dimensional projection dose data acquired at that energy value. In an exemplary embodiment, the source can be configured to generate radiant energy x-ray beams at various energies. For example, and without limitation, the source can be a dual-energy source. By utilizing dual energies, the inspection system 100 can distinguish between materials having different density and atomic properties, such as, and without limitation, organic, inorganic, and metallic materials. Because organic materials such as body tissue and clothing, are typically less dense than inorganic and metallic materials, they can attenuate fewer of the contributions to the incident x-ray beam, whereas more dense, relatively high-atomic number inorganic and metallic materials can attenuate relatively more of the available x-ray energy. By comparing high-energy and low-energy absorption patterns, the x-ray scanning can be effective at imaging different types of materials, including, for example, those concealed on or in the body of the individual being scanned.

In an embodiment, the individual can be subject to a high-energy x-ray beam scanned rapidly over their body. During each scan, the second sensing apparatus can collect multiple sets of projection data representative of the detected signal strength of the transmitted x-ray. The second sensing apparatus can use the projection data to generate a signal related to subject dose data. The signal related to subject dose data can be representative of the intensity of the radiant energy absorbed or attenuated by the individual and can be used for forming the raster lines of a two-dimensional projection image. The second sensing apparatus can be configured to identify portions of the scanning volume where the attenuated radiant energy is below a threshold energy measurement, indicating insufficient energy measurements which can necessitate adjustment of the dose of radiant energy applied to the scanning volume.

In an embodiment, a third radiant sensing apparatus can be configured to sense the radiant energy reflected back or deflected off of an individual or item being scanned, i.e., backscatter x-ray radiation. The third sensing apparatus can be oriented such that its detection surface is directed towards the scanning volume. Because elements with lower atomic number scatter protons with greater magnitude, backscatter x-ray methods such as the disclosed embodiment, are effective at imaging organic materials, such as the body surface of the individual being scanned. In an embodiment, the individual can be subject to a high-energy x-ray beam scanned rapidly over their body. During each scan, the third sensing apparatus can collect multiple sets of projection data representative of the detected signal strength of the backscattered x-ray photons. The third sensing apparatus can use the projection data to generate a signal related to subject dose data representative of the intensity of the radiant energy reflected from the individual and that can be used for forming the raster lines of a two-dimensional projection image. Therefore, as the individual passes through the scanner 110, a two-dimensional projection image of the body surface of an individual can be formed as a function of the x-ray energy from the two-dimensional projection dose data acquired at that energy value. The third sensing apparatus can be configured to identify portions of the scanning volume where the reflected radiant energy is below a threshold energy measurement, indicating insufficient energy measurements which can necessitate adjustment of the dose of radiant energy applied to the scanning volume.

In an embodiment, there can be a one-to-one relationship between radiation sources and a first and second sensing apparatuses (i.e., two sources, two first sensing apparatuses, and two second sensing apparatuses). It is also contemplated that scanner 110 can be implemented with any number of moveable or rotatable sources and/or sensing apparatuses in a one-to-one or one-to-many relationship to illuminate the individual being scanned. It is contemplated that the radiation source and the sensing apparatuses can be positioned directly opposing one another, in a parallel configuration. It is also contemplated that the radiation source and the sensing apparatuses can be positioned opposing each other in a non-parallel configuration. For example, in an exemplary embodiment consistent with the disclosure, the source can be positioned at a height 30" to 60" above conveyance apparatus 120 and a portion of the sensing apparatus can be positioned at a height less than 30" to 60" above conveyance apparatus 120. The source, therefore, can emit radiant energy at a declining angle towards a portion of the sensing apparatus through the approximate midsection of an individual's body. The radiant energy proceeds through the individual's body at an angle and the resultant image of the individual's midsection appears "stretched," thereby allowing threat objects in this region to be distinguished with higher efficiency. It is contemplated, however, that additional sensors associated with the sensing apparatus can extend both above and below the 30" to 60" height described above.

It is also contemplated that the radiation source and sensing apparatus can be modular or can comprise modular components, allowing for ease of replacement of defective or damaged components.

In an exemplary embodiment, the scanner 110 can also, actively or passively, examine the individual or scanning volume for radioactive material, gamma radiation, or neutron detection. For example, scanner 110 can detect radioactive material concealed under the clothing of the individual being scanned In an embodiment, a dose controller can be configured to acquire conveyance data, source radiant energy data, and a signal related to subject dose data. Using the received data, the dose controller can determine whether the individual has been subjected to a dose of radiant energy above a maximum threshold value. In an embodiment, the dose of radiant energy acquired by the individual is in the range of 0 to 4.5 μSv or 0 to 2.0 μSv, and ideally less than 0.1 μSv.

It is also contemplated that the dose controller can be configured to generate dose instructions for altering the function of the source, the filter, and conveyance apparatus 120. In one embodiment, the dose controller is a real-time controller and the dose instructions can be generated in real-time. As used herein, the adjective "real-time," in connection with a scanned object, such as an individual, and a scanning system, such as the disclosed inspection system 100, means of or relating to a time interval that is shorter or approximately equivalent to the time interval required to convey the individual through the inspection system 100 (such a time interval consistent with the present disclosure, for exemplary purposed only, and without limitation, can be within a range from milliseconds to a few seconds). It is also contemplated that the dose instructions can also utilize data received from a data processor 130 and/or operator input when generating the dose instructions.

In an embodiment, the dose controller can be configured to generate dose instructions to the scanner 110. The source, in response to the dose instructions, can be configured to vary the dose energy level and/or the direction of the radiant energy applied to the scanning volume. The dose controller can also be configured to generate different dose instructions to various source and sensing apparatus pairs. The source and sensing apparatus pairs can be separately activated according to the desired mode/function of the inspection system 100. In an exemplary embodiment, the dose controller can be configured to generate dose instructions for application to the filter. Adjusting the filter can include adjusting the filter to modify the energy, density, and direction of the radiant energy applied to the scanning volume. It is also contemplated that the scanning volume can be adjusted by modifying the filter. For example, and without limitation, a layer of material, such as polyethylene material, can be included or added to inspection system 100 and situated between the source and the inspection compartment 112 in order to further attenuate radiation from the source in a selected range from reaching the inspection compartment 112. In an exemplary embodiment, the dose controller can be configured to generate updated conveyance instructions for conveyor 122. Conveyance instructions can include, for example, instructions to vary the direction, speed, and/or acceleration of the conveyor 122 through scanner 110.

The dose controller can be configured to acquire conveyance apparatus fault data, source fault data, and subject fault data. In response to conveyance apparatus 120, source, and filter fault data, inspection system 100 can be configured to cease operation. Conveyance apparatus fault data may include, for example, indication of conveyor 122 malfunction or unauthorized movement of the individual within the scanning volume. It is contemplated that inspection system 100 may include components configured to indicate an unauthorized movement of the individual, such as, for example, pressure sensitive electronics, infra-red detectors, optical beams, and motion cameras. It is also contemplated, that an operator or the individual may cease operation of conveyance apparatus 120 by providing an indication to the dose controller, such as, for example, triggering an emergency stop sequence. Source fault data may include, for example, indication of overload of the radiation source, power failure, and radiation source or detector malfunction.

The data processor 130 can be coupled to the scanner 110 and the conveyance apparatus 120 via, for example, one or more data transmission lines 132. The source radiant energy data, the signal related to subject dose data, and the conveyance data can be transferred to the data processor 130 via the data transmission lines 132. In one embodiment, data can be wirelessly transferred to the data processor 130 to enable, for example a remote screening application or a cloud networked application.

The data processor 130 can include a processor, memory, a dose controller interface, a storage device, an input/output interface 134, and a display device 136. The data processor 130 can include additional, fewer, and/or different components than those listed above. The type and number of listed components are exemplary only and not intended to be limiting.

The processor can be a central processing unit(s) (CPU) and/or a graphic processing unit(s) (GPU). The processor can execute sequences of computer program instructions to perform various computation and analysis processes. The memory modules include, among other things, a random access memory (RAM) and a read-only memory (ROM). The computer program instructions can be accessed and read from the ROM, or any other suitable memory location, and loaded into the RAM for execution by the processor. Depending on the type of the data processor 130 being used, the processor can include one or more printed circuit boards, and/or microprocessor chips, or may have the form of a multi-processor industrial computer or a combination of several independent rack computers optimized for different processing tasks such as image analysis, detection algorithm processing, and image presentation.

The scanner control interface can be configured for two-way communication between the dose controller and data processor 130. In an embodiment, the scanner control interface can be configured to receive scan data from the dose controller and store the data onto a storage device. The scanner control interface can also be configured to send scan instructions to modular scanner 110 to initiate, stop, or otherwise configure modular scanner 110 operation. For example, scan instructions can include stop instructions in the event the operator has identified a fault situation. Scan instructions can also include instructions for varying the "mode" of scanner 110, such as, for example, Full, Torso, or Body Scan Mode. In an exemplary embodiment, the various scanner modes can include source-sensing apparatus configurations wherein source-sensing apparatus pairs can be jointly or separately activated, at similar or different energies.

The conveyer control interface can also be configured for two-way communication between conveyance system 120 and the dose controller. In an embodiment, the conveyor control interface can be configured to receive information from conveyance system 120 and store the data on a storage device. The conveyor control interface can also be configured to send conveyance instructions to the dose controller to initiate, stop, or otherwise modify conveyance system 120 operation. For example, conveyance instructions may include conveyor 122 speed settings or conveyer 122 malfunction information.

The data processor 130 can also visually display information to a user or operator via display device 136. Display device 136 can include, for example, a computer screen that provides a graphical user interface (GUI) to the operator. Consistent with an embodiment, display device 136 can display a scan image of the subject passenger, such as, for example, a two-dimensional projection image of the scanning region. The scan image can depict different colors or contrast to indicate signal strength of the x-ray radiation transmitted through various portions of the subject passenger. Where reflected radiation is detected, the scan image can also, or alternatively, depict different colors or contrast to indicate signal strength of the reflected radiation. The data processor 130 can process the signal related to subject dose data and determine optimal image presentation parameters (color palette, contrast, etc.). It is contemplated that data processor 130 can provide tools for the operator to enhance or otherwise manipulate the scan image in response to operator preferences. For example, in an embodiment, the operator can adjust the scan image brightness, enlarge select areas of the scan image, and switch between a negative and positive exposure of the scanned image. The data processor 130 can also display on display device 136 an indication of the applied image filters or enhancements. Filter options may include, for example, frequency dependent contrast modification (frequency enhancement processing), automatic gradation processing, pseudo-coloring of gray scale image, and edge enhancement. It is also contemplated that the data processor 130 can be configured to enable the operator to view various manipulated and non-manipulated scan images simultaneously or individually.

In an embodiment, the data processor 130 can identify areas within the scanning region with excess x-ray absorption based upon scan data received from scanner 110. For example, the data processor 130 can provide the operator with an excess absorption notification, referred to, for example, as a "dark alarm," and/or image fault notification. Based on the scan data, data processor 130 can provide dose instructions to the scanner control interface and/or the conveyor control interface, either automatically or in response to operator input.

The storage device can include any type of mass storage device suitable for storing information. For example, the storage device can include one or more hard disk devices, optical disk devices, or any other storage devices that provide data storage space. In one embodiment of the present disclosure, the storage device can store data related to the data processing process, such as the scan data received from scanner 110 of conveyance data received from conveyance apparatus 120, and any intermediate data created during the data processing process. The storage device can also include analysis and organization tools for analyzing and organizing the information contained therein.

The data processor 130 can be accessed and controlled by a user via input/output interface 134. The input/output interface 134 can allow the operator to input information which can be analyzed by the data processor 130, and can include, for example, a keyboard, a mouse, a touch screen, and/or optical or wireless computer input devices. The operator can input control instructions via the input/output interface 134 to control the operation of the scanner 110 and the conveyance apparatus 120. The operator can also make and store notes and any other data relevant to inspection system 100. Similarly, the operator can manually input parameters that adjust the operation of the conveyor 122 and one or more of the radiation sources such as, for example, in a fault situation or when initiating an emergency sequence.

Figure 3A:
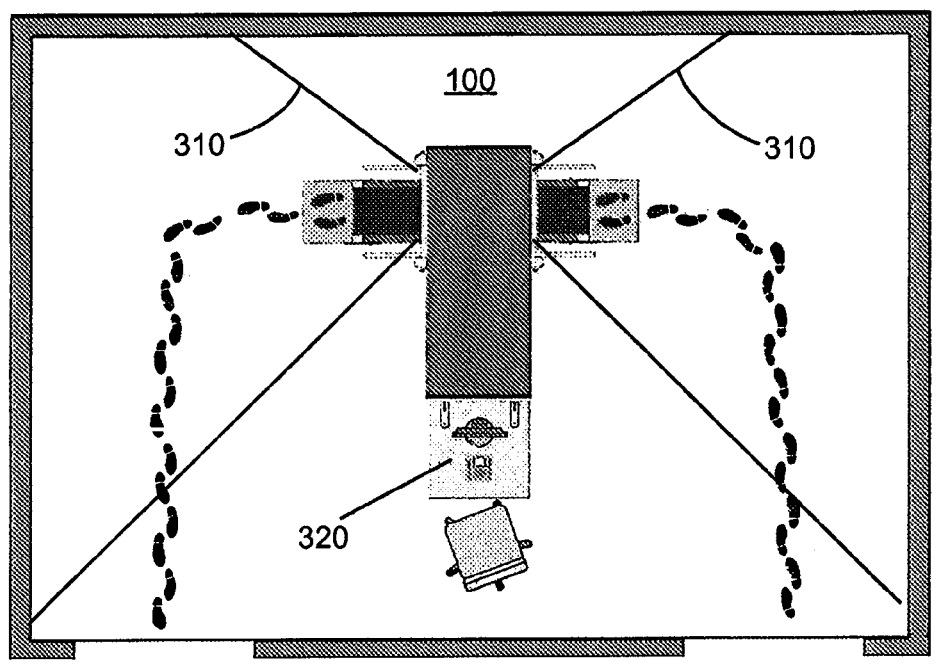
FIGS. 3A-B depict a schematic diagram of radiation distribution consistent with an exemplary embodiment of the present disclosure.
Figure 3B:
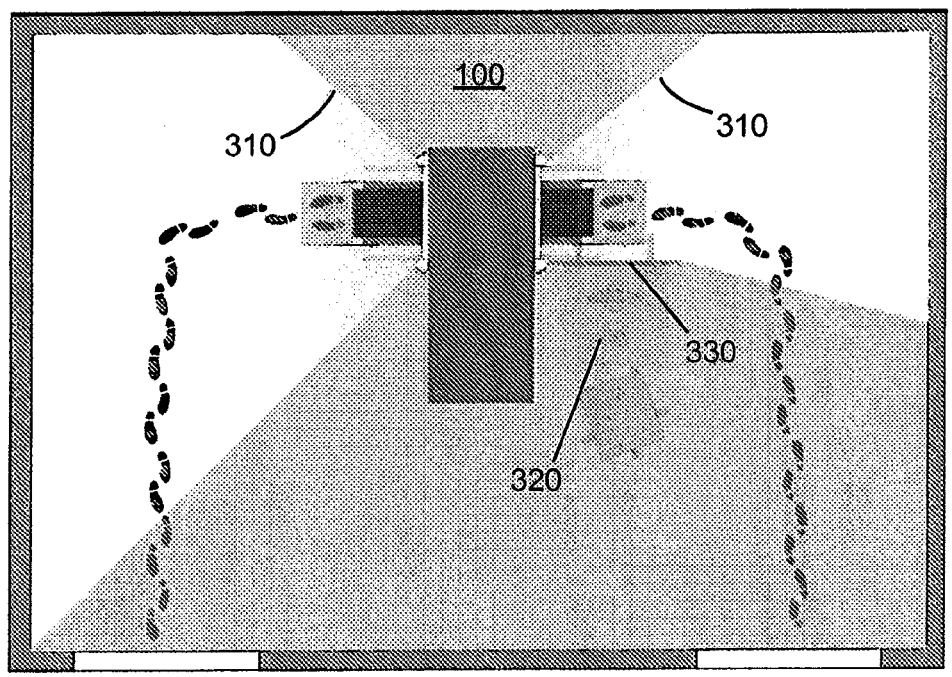

FIG. 3A provides a schematic diagram of the radiation distribution consistent with an embodiment. The radiation exposure to the operator can be limited. As illustrated in FIG. 3A, area 310 indicates the region outside of the inspection system 100 that is exposed to scattered radiation during x-ray inspection. To ensure limited operator exposure, an operator workspace 320 can be located at a position outside of area 310, and is therefore, not exposed to scattered radiation. FIG. 3B provides an schematic diagram of the radiation distribution consisted with an exemplary embodiment including radiation protection walls 330 as a method shielding the operator workspace 320 from scattered radiation. As illustrated in FIG. 3B, the inclusion of the radiation protection walls 330 modifies the form of the area 310, narrowing the region outside of the inspection system 100 that can be exposed to scattered radiation during x-ray inspection. The embodiment illustrated in FIG. 3B can provide an alternate configuration of the inspection system 100 and the operator workspace 320. It is contemplated that additional, fewer, and/or different radiation protection walls 330 may be used to further modify the form of area 310 and provide further configurations of inspection system 100 and operator workspace 320.

Figure 4A:
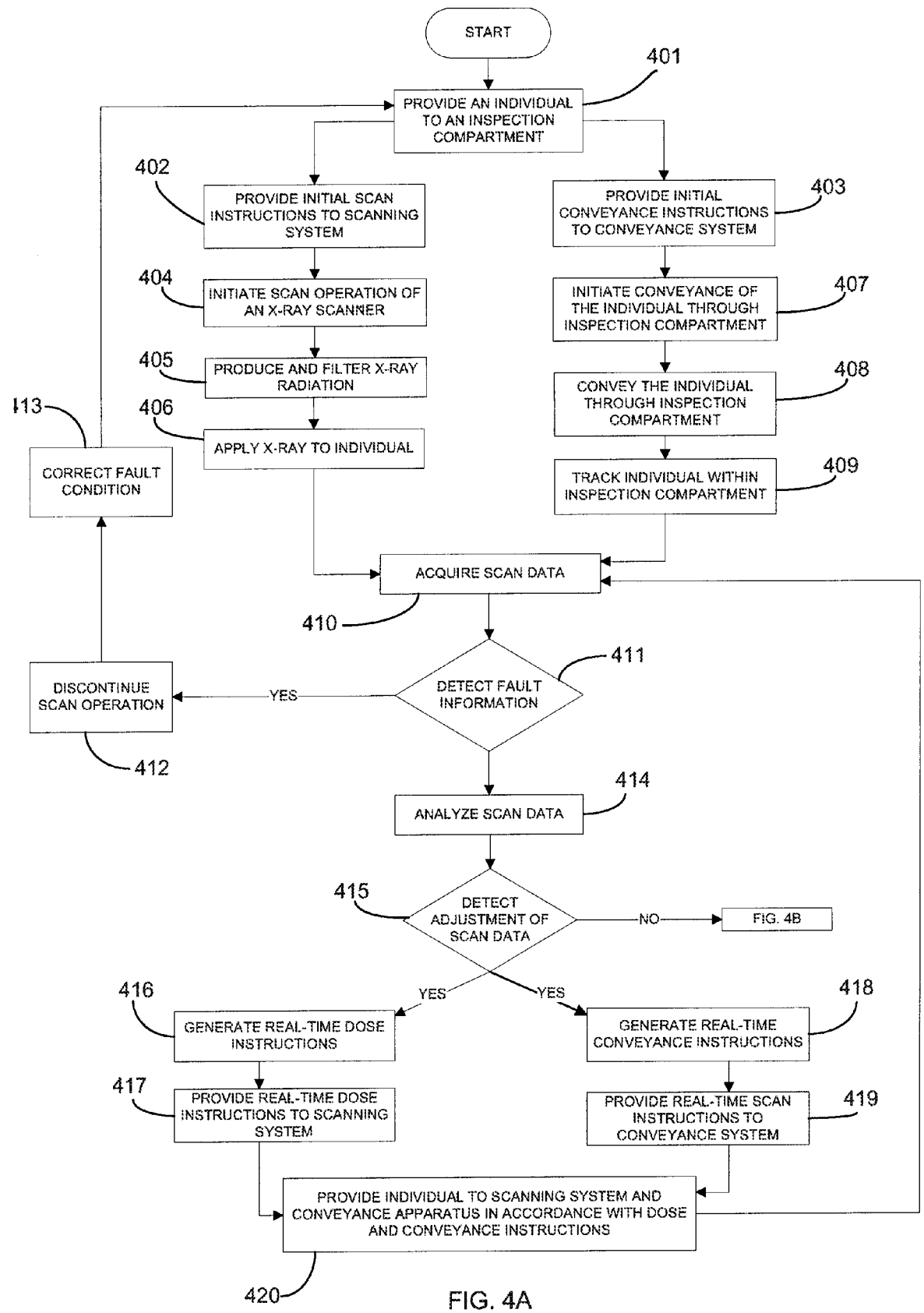
FIGS. 4A-4B depict a flow chart of an exemplary process of scanning an individual utilizing an inspection system, consistent with the present disclosure.
Figure 4B:
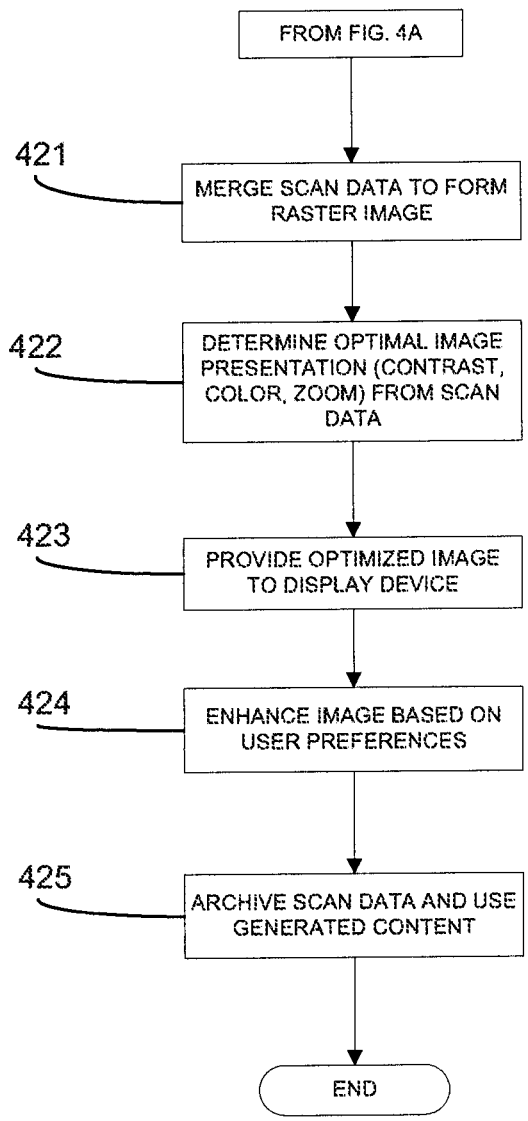

FIGS. 4A and 4B provide a flow chart of an exemplary process of scanning an individual utilizing an inspection system, consistent with the embodiment of FIG. 1.

An individual can be provided to an inspection compartment of an x-ray scanner (Step 401). Initial scan instructions and initial conveyance instructions can be provided to the scanning system (Step 402) and the conveyance system (Step 403) respectively. Once the individual is provided to the inspection compartment and initial scan instructions are received, a scan operation of the x-ray scanner can be initiated (Step 404) by the scanning system. Initiation of the scan operation prior to the individual's entry into the inspection compartment can be prohibited. During the scan operation, x-ray radiation beams are produced and filtered (Step 405). While filtering the x-ray radiation, the produced radiant energy is separated into a portion to be transmitted to the scanning volume and a portion to be blocked from the scanning volume. In the embodiment, the radiant energy transmitted to the scanning volume can have a higher x-ray energy than the portion blocked from the scanning volume. The filtered x-ray radiation beams are directed towards and applied to the individual (Step 406) in accordance with the scan instructions.

Once the individual has been provided to the inspection compartment and initial conveyance instructions, the conveyance system can initiate the conveyance of the individual through the inspection compartment (Step 407). The individual can then be conveyed through the inspection compartment and the scanning volume in accordance with the conveyance instructions (Step 408). The location and movement of the individual within the inspection compartment can be tracked relative to the conveyance instructions (Step 409). During conveyance and tracking, conveyance data is collected, including, for example, conveyance state data. Using the conveyance state data, the inspection system can confirm the location of the individual in accordance with the conveyance instructions and can also identify instances where the individual is in a location not in accordance with the conveyance instructions, such as, for example, if the individual were to step out of the inspection compartment. It is contemplated that x-ray scanning of the individual and conveyance of the individual through the inspection compartment can occur simultaneously.

The scanner can acquire source radiant energy data and a signal related to subject dose data, associated with the inspection region and individual, by applying an x-ray radiation beam at various energies and in various views in accordance with the initial scan instructions (Step 410). The inspection system may detect fault information, such as, for example, source fault data, dose fault data, and conveyance apparatus fault data indicative of a fault indicated by the source radiant energy data, the signal related to subject dose data, the conveyance data, an indication associated with the individual being scanned, and/or operator input. In an exemplary embodiment, the conveyance apparatus fault data can be indicative of a fault associated with the individual being scanned, operator input, and/or conveyance state information, such as, for example, conveyor motor failure or conveyor belt malfunction. If fault information is detected, the inspection system can terminate scan and conveyance operations (Step 412) and can be configured to refrain from resuming operation until the fault condition has been corrected (Step 413).

Scan data can be analyzed by the dose controller (Step 414) to determine whether an adjustment of the scan data is required (Step 415). An adjustment can be required, for example, where a portion of the data indicates excess x-ray absorption by the individual. It is also contemplated that the data processor 130 and/or the operator can determine whether adjustment of the source, filter, and/or conveyance apparatus is necessary.

Adjustment of the source, filter, and/or conveyance apparatus can be accomplished by varying the conveyance instructions and/or the dose instructions. The dose controller can provide instructions to the conveyance apparatus, the source, and/or the filter to adjust the energy level of the produced x-ray radiation beam, the scan speed, and/or exposure time in accordance with the properties of the scanner volume (Step 416, Step 417). Additionally, the conveyance apparatus, in response to the conveyance instructions can be configured to adjust the speed and/or direction of the individual through the scanning volume (Step 418, Step 419). The dose controller can then adjust the scan speed and x-ray dose to accommodate for any necessary adjustments (Step 420). In this manner, the inspection system can provide updated scan data adequate to produce scan images that benefit from the updated configuration. The acquired data can then be analyzed to determine whether additional modification to the scan and conveyance instructions is necessary. The acquired data can also be analyzed to determine whether the individual has been exposed to a radiation dose above a maximum threshold value.

It is also contemplated that the scanning system and the conveyance apparatus can be configured to receive operator input adjusting the conveyor and scanner respectively. In an embodiment, using the data processor 130, the operator can view, analyze, and adjust the configuration of the scanner system and the conveyor system. It is also contemplated that the data processor 130 can adjust the conveyance instruction and the dose instruction. Once the conveyance instructions and dose instruction have been adjusted based on operator input and data processor analysis, the individual is rescanned and new scan data can be acquired (Step 420).

Once it is determined that no further modification to the scan configuration is necessary, the data processor 130 can merge the scan data to form an image for display to the operator (Step 421). Based on the merged scan data, the data processor 130 can determine optimal image presentation parameters, including image contrast and color (Step 422). The data processor 130 can provide the optimized image to the display device (Step 423). The data processor 130 and/or the operator can determine whether additional modification to the image is necessary (Step 424). The operator can, for example, prefer to resize the image, filter the image, and adjust the color or contrast of the image. Similarly, it is contemplated that using the data processor, the operator can view, analyze, and adjust data associated with the passenger, the configuration of the scanning system and conveyor system, current and historic scan data, current and historic fault information, and any other data or parameters stored on the processor (Step 425).

Advantages of the inspection system 100 as disclosed herein can include, low dose x-ray imaging and an adjustable equipment footprint including adjustable radiation shielding to prevent operator exposure to radiation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system configured to expose a target to x-ray radiation, the system comprising:
    at least one source of radiant energy, where at least a first portion of the radiant energy lies within an x-ray spectrum, and where the source is configured so that the first portion of the radiant energy traverses at least a portion of a scanning volume;
    a filter situated between the source and the portion of the scanning volume;
    a conveying apparatus configured to impart relative motion between an exposure-limited subject and the portion of the scanning volume;
    a conveyance monitor configured to generate conveyance data reflecting at least a conveyance state of the exposure-limited subject;
    a first radiant energy sensing apparatus configured to sense radiant energy from the source and to generate source radiant energy data;
    a dose controller configured to acquire conveyance data, source radiant energy data, and a signal related to subject dose data, and to generate a measure that at least a portion of the exposure-limited subject has acquired a dose of radiant energy above a dose threshold; and
    wherein the dose of radiant energy is representative of an amount of radiant energy absorbed by the exposure-limited subject.

2. The system of claim 1, further comprising: a second radiant energy sensing apparatus configured to sense at least a portion of radiant energy attenuated by the exposure-limited subject and configured to generate the signal related to subject dose data.

3. The system of claim 2, wherein the at least one source comprises a first source and a second source.

4. The system of claim 1, wherein the dose controller is configured to produce a radiographic image based on the signal related to subject dose data and the measure.

5. The system of claim 1, wherein the radiant energy is collimated into a thin fan-shaped beam of radiant energy.

6. The system of claim 1, wherein the source of radiant energy produces high-energy and low-energy x-ray radiation.

7. The system of claim 1, wherein the filter is configured to separate the first portion of the radiant energy into at least a transmit portion and a limit portion.

8. The system of claim 7, wherein an energy level of the x-ray spectrum associated with the limit portion is less than an energy level of the x-ray spectrum associated with the transmit portion.

9. The system of claim 1, wherein the filter comprises an effective filter.

10. The system of claim 9, wherein the at least one source of radiant energy has an energy of approximately 160 kV, and the effective filter has an aluminum equivalent greater than approximately 1.5 mm.

11. The system of claim 10, wherein the effective filter comprises at least one material selected from the set of: glass, oil, epoxy, titanium, aluminum, polyethylene, and stainless steel.

12. The system of claim 1, wherein the conveyance data includes conveyance apparatus fault data, where upon initiation of conveyance apparatus fault data the conveyance apparatus is configured to cease operation.

13. The system of claim 1, wherein the conveyance state include direction and conveyance speed data of the exposure-limited subject.

14. The system of claim 1, wherein the source radiant energy data includes information indicative of an energy level of the x-ray spectrum associated with the source.

15. The system of claim 1, wherein the source radiant energy data includes at least one of source fault data and subject dose fault data.

16. The system of claim 15, wherein upon initiation of at least one of source fault data and subject dose fault data, the source is configured to cease operation.

17. The system of claim 2, wherein the second radiant energy sensing apparatus is further configured to sense at least one of stereoscopic gamma radiation and neutron radiation.

18. The system of claim 1, wherein the dose controller is further configured to generate dose instructions for altering at least one of the source, the filter, and the conveyance apparatus, where the dose instructions are based on at least one of the conveyor data, the source radiant energy data, the signal related to subject dose data, the measure, and a user input.

19. The system of claim 1, wherein the dose controller is further configured to generate conveyance instructions for altering the at least one of a conveyance direction and a conveyance speed of the conveyance apparatus, where the conveyance instructions are based on least one of the conveyor data, the source radiant energy data, the signal related to subject dose data, the measure, and a user input.

20. The system of claim 1, wherein the dose threshold is about 4.5 µSv.

21. The system of claim 1, wherein the dose threshold is about 2.0 µSv.

22. The system of claim 1, wherein the dose threshold is less than about 0.1 µSv.

23. A method for scanning an exposure-limited subject comprising:
producing at a source, radiant energy within a defined x-ray spectrum;
providing the radiant energy in a direction that traverses at least a portion of a scanning volume;
filtering the radiant energy with a filter to produce filtered radiant energy;
applying at least a portion of the filtered radiant energy to the scanning volume;
conveying the exposure-limited subject to the scanning volume and generating conveyance data indicative of at least a conveyance state of the exposure-limited subject;
applying at least a portion of the filtered radiant energy to the exposure-limited subject;
sensing the radiant energy produced from the source and generating source radiant energy data;
acquiring conveyance data, source radiant data, and a signal related to subject dose data at a dose controller and generating a measure indicative of the dose of radiant energy acquired by the exposure-limited subject, where the measure indicates when the dose of radiant energy acquired by the exposure-limited subject is above a dose threshold; and
adjusting at least one of the production of radiant energy, the filtering of radiant energy, and the conveying in response to at least one of the conveyance data, the source radiant data, and the signal related to subject dose data, and the measure.

24. The method of claim 23, further comprising sensing the radiant energy attenuated by the exposure-limited subject and generating the signal related to subject dose data.

25. The method of claim 23, wherein producing radiant energy at a source is initiated by entry of the exposure-limited subject into the scanning volume and ceases upon exit of the exposure-limited subject from the scanning volume.

26. The method of claim 23, wherein producing radiant energy includes producing high-energy and low-energy radiation.

27. The method of claim 23, wherein producing radiant energy further comprises collimating the radiant energy into a thin fan-shaped beam of radiant energy.

28. The method of claim 23, wherein filtering the radiant energy comprises separating the radiant energy into a transmit portion and a limit portion, where the transmit portion is applied to the exposure-limited subject.

29. The method of claim 23, wherein an energy level of the x-ray spectrum associated with the limit portion is less than an energy level of the x-ray spectrum associated with the transmit portion.

30. The method of claim 23, wherein the filter comprises an effective filter.

31. The method of claim 30, wherein the source has an energy of approximately 160 kV, and the effective filter has an aluminum equivalent greater than approximately 1.5 mm.

32. The method of claim 31, wherein the effective filter comprises at least one material selected from the set of: glass, oil, epoxy, titanium, aluminum, polyethylene, and stainless steel.

33. The method of claim 23, wherein generating conveyance data includes generating conveyance fault data.

34. The method of claim 23, wherein generating conveyance data includes determining at least one of the conveyance direction and speed.

35. The method of claim 23, wherein conveying the exposure-limited subject to the scanning volume includes tracking a position of the exposure-limited subject relative to the scanning volume.

36. The method of claim 23, wherein applying a least a portion of the filtered radiant energy to the exposure-limited subject further includes applying low dose of radiant energy.

37. The method of claim 36, wherein the dose threshold is about 4.5 μSv.

38. The method of claim 36, wherein the dose threshold is about 2.0 μSv.

39. The method of claim 36, wherein the dose threshold is less than about 0.1 μSv.

40. The method of claim 23, wherein generating source radiant energy data includes determining a produced energy level of the defined x-ray spectrum associated with the source.

41. The method of claim 23, wherein generating the source radiant energy data and generating the signal related to subject dose data further includes generating radiant energy fault data and subject dose fault data.

42. The method of claim 24, wherein sensing the radiant energy attenuated by the exposure-limited subject further includes sensing at least one of stereoscopic gamma radiation and neutron radiation.

43. The method of claim 23, wherein adjusting the production of radiant energy further includes adjusting at least one of the energy level and the direction of the radiant energy.

44. The method of claim 43, wherein adjusting at least one of the energy level and the direction of the radiant energy includes providing radiant energy at various energy levels and various directions.

45. The method of claim 23, wherein adjusting the filtering of radiant energy further comprises adjusting at least one of the energy, intensity, and direction of the radiant energy.

46. The method of claim 23, wherein adjusting the filtering of radiant energy further comprises adjusting a portion of the scanning volume.

47. The method of claim 23, wherein adjusting the conveying further includes adjusting at least one of the conveyance direction and speed.

48. The method of claim 23, wherein adjusting further includes ceasing all production, filtering, and conveying upon initiation of at least one of conveyance fault data, energy fault data, and subject dose fault data.

49. The method of claim 23, further comprising producing a radiographic image based on the signal related to subject dose data and the measure.

50. The method of claim 49, wherein producing a radiographic image further comprises processing the signal related to subject dose data to enhance the radiographic image.

51. The method of claim 49, further comprising storing the radiographic image in a database and retrieving the radiographic image from the database.

* * * * *